(12) United States Patent
Sigurdsson et al.

(10) Patent No.: US 12,263,108 B2
(45) Date of Patent: *Apr. 1, 2025

(54) SLEEVE AND METHOD FOR USE WITH ORTHOPEDIC DEVICE

(71) Applicant: Ossur Iceland ehf, Reykjavik (IS)

(72) Inventors: Sindri Pall Sigurdsson, Reykjavik (IS); Hronn Kristinsdottir, Reykjavik (IS); Christophe Valois, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 18/541,842

(22) Filed: Dec. 15, 2023

(65) Prior Publication Data

US 2024/0108489 A1   Apr. 4, 2024

Related U.S. Application Data

(63) Continuation of application No. 17/559,820, filed on Dec. 22, 2021, now Pat. No. 11,872,150.
(Continued)

(51) Int. Cl.
*A61F 5/01* (2006.01)

(52) U.S. Cl.
CPC ................... *A61F 5/0109* (2013.01)

(58) Field of Classification Search
CPC .... A61F 5/0109; A61F 5/0123; A61F 5/0125; A61F 5/0106; A61F 2005/0176;
(Continued)

(56) References Cited

U.S. PATENT DOCUMENTS

| 667,768 | A | 2/1901 | Puy |
| 777,585 | A | 12/1904 | Beatty |

(Continued)

FOREIGN PATENT DOCUMENTS

| CN | 1354643 A | 6/2002 |
| CN | 2604894 A1 | 3/2004 |

(Continued)

OTHER PUBLICATIONS

"VELSTICK semi-rigid Fastener Furnished in Separate, Mating Components", Velcro Fasteners, Spaenaur, Sep. 2, 2009, 1 Page.

(Continued)

*Primary Examiner* — Camtu T Nguyen
(74) *Attorney, Agent, or Firm* — Workman Nydegger

(57) ABSTRACT

A sleeve has a tubular body formed from an elasticized textile and has first and second ends. The first end defines a locking cuff having a tacky band extending about an exterior surface of the sleeve; a non-tacky band located adjacent to and extending distally from the tacky band; and a receiving band located adjacent to and extending distally from the non-tacky band. The textile body further defines a central portion adjacent to and extending distally from the receiving band to the second end. The central portion includes an anatomical band arranged to contour to the anatomy of a user having at least one different elastic property different from an elastic property of the central portion outside of the anatomical band.

8 Claims, 4 Drawing Sheets

Related U.S. Application Data

(60) Provisional application No. 63/130,978, filed on Dec. 28, 2020.

(58) Field of Classification Search
CPC ..... A61F 2005/0165; D04B 1/18; D04B 1/04; D04B 1/265; D04B 1/14; D10B 2403/032; D10B 2501/061; D10B 2509/028; A41D 31/18; A41D 13/0002; A41D 2600/00; A41D 13/08

See application file for complete search history.

(56) References Cited

U.S. PATENT DOCUMENTS

| | | |
|---|---|---|
| 937,478 A | 10/1909 | Sims |
| 1,153,334 A | 9/1915 | Oswald |
| 1,227,700 A | 5/1917 | Tucker |
| 1,328,541 A | 1/1920 | Palmer |
| 1,510,408 A | 9/1924 | Lychou |
| 1,529,928 A | 3/1925 | Schuster |
| 1,593,631 A | 7/1926 | Harsh |
| 1,622,211 A | 3/1927 | Sheehan |
| 1,825,898 A | 10/1931 | Coulter |
| 1,965,314 A | 7/1934 | Henderson |
| 2,032,923 A | 3/1936 | Eldridge |
| 2,179,903 A | 11/1939 | Spears |
| 2,186,572 A | 1/1940 | Boepple |
| 2,467,907 A | 4/1949 | Peckham |
| 2,573,866 A | 11/1951 | Murphy |
| 2,717,841 A | 9/1955 | Biefeld et al. |
| 2,935,065 A | 5/1960 | Homier et al. |
| 3,031,730 A | 5/1962 | Morin |
| 3,046,981 A | 7/1962 | Biggs, Jr. et al. |
| 3,059,834 A | 10/1962 | Hausammann |
| 3,089,486 A | 5/1963 | Pike |
| 3,255,613 A | 6/1966 | Burd |
| 3,266,113 A | 8/1966 | Flanagan, Jr. |
| 3,306,081 A | 2/1967 | Miles et al. |
| 3,463,147 A | 8/1969 | Stubbs |
| 3,478,748 A | 11/1969 | Bjorn-Larsen |
| 3,496,944 A | 2/1970 | Cuozzi |
| 3,514,313 A | 5/1970 | Martel et al. |
| 3,520,765 A | 7/1970 | Bateman |
| 3,528,412 A | 9/1970 | McDavid |
| 3,581,741 A | 1/1971 | Rosman |
| 3,561,436 A | 2/1971 | Gaylord, Jr. |
| 3,594,863 A | 7/1971 | Erb |
| 3,594,865 A | 7/1971 | Erb |
| 3,638,658 A | 2/1972 | Becker et al. |
| 3,742,557 A | 7/1973 | Francois |
| 3,752,619 A | 8/1973 | Menzin et al. |
| 3,758,657 A | 9/1973 | Menzin et al. |
| 3,789,842 A | 2/1974 | Froimson |
| 3,804,084 A | 4/1974 | Lehman |
| 3,817,244 A | 6/1974 | Taylor |
| 3,851,357 A | 12/1974 | Ribich et al. |
| 3,877,426 A | 4/1975 | Nirschl |
| 3,916,077 A | 10/1975 | Damrau |
| 3,927,881 A | 12/1975 | Lemelson et al. |
| 3,945,046 A | 3/1976 | Stromgren |
| 3,955,565 A | 5/1976 | Johnson, Jr. |
| 3,975,929 A | 8/1976 | Fregeolle |
| 4,130,115 A | 12/1978 | Taylor |
| 4,176,665 A | 12/1979 | Terpening |
| 4,193,395 A | 3/1980 | Gruber |
| 4,201,203 A | 5/1980 | Applegate |
| 4,204,532 A | 5/1980 | Lind et al. |
| 4,240,414 A | 12/1980 | Theisler |
| 4,269,179 A | 5/1981 | Burton et al. |
| 4,269,181 A | 5/1981 | Delannoy |
| 4,275,716 A | 6/1981 | Scott, Jr. |
| 4,280,489 A | 7/1981 | Johnson, Jr. |
| 4,291,072 A | 9/1981 | Barrett et al. |
| 4,296,744 A | 10/1981 | Palumbo |
| 4,304,560 A | 12/1981 | Greenwood |
| 4,312,335 A | 1/1982 | Daniell, Jr. |
| 4,336,279 A | 6/1982 | Metzger |
| 4,372,298 A | 2/1983 | Lerman |
| 4,379,463 A | 4/1983 | Meier et al. |
| 4,381,768 A | 5/1983 | Erichsen et al. |
| 4,381,769 A | 5/1983 | Prahl |
| 4,386,723 A | 6/1983 | Mule |
| 4,396,012 A | 8/1983 | Cobiski |
| 4,466,428 A | 8/1984 | McCoy |
| 4,470,857 A | 9/1984 | Casalou |
| 4,472,461 A | 9/1984 | Johnson |
| 4,492,227 A | 1/1985 | Senn et al. |
| 4,506,661 A | 3/1985 | Foster |
| 4,528,440 A | 7/1985 | Ishihara |
| 4,554,913 A | 11/1985 | Womack et al. |
| 4,556,053 A | 12/1985 | Irons |
| 4,572,170 A | 2/1986 | Cronk et al. |
| 4,617,214 A | 10/1986 | Billarant |
| 4,632,098 A | 12/1986 | Grundei et al. |
| 4,677,713 A | 7/1987 | Copp |
| 4,693,921 A | 9/1987 | Billarant et al. |
| D292,529 S | 10/1987 | Saare |
| 4,697,583 A | 10/1987 | Mason et al. |
| 4,724,831 A | 2/1988 | Huntjens |
| 4,768,500 A | 9/1988 | Mason et al. |
| 4,775,310 A | 10/1988 | Fischer |
| D298,568 S | 11/1988 | Womack et al. |
| 4,782,605 A | 11/1988 | Cahpnick |
| 4,791,916 A | 12/1988 | Paez |
| 4,794,028 A | 12/1988 | Fischer |
| 4,801,138 A | 1/1989 | Airy et al. |
| 4,802,939 A | 2/1989 | Billarant et al. |
| 4,805,606 A | 2/1989 | McDavid, III |
| 4,854,308 A | 8/1989 | Drillio |
| 4,856,501 A | 8/1989 | Castillo et al. |
| 4,856,502 A | 8/1989 | Ersfeld et al. |
| 4,870,956 A | 10/1989 | Fatool et al. |
| 4,872,243 A | 10/1989 | Fischer |
| 4,908,037 A | 3/1990 | Ross |
| 4,922,929 A | 5/1990 | DeJournett |
| 4,933,035 A | 6/1990 | Billarant et al. |
| 4,953,543 A | 9/1990 | Grim et al. |
| 4,961,544 A | 10/1990 | Bidoia |
| 4,966,133 A | 10/1990 | Kausek |
| 4,989,593 A | 2/1991 | Campagna et al. |
| 4,991,574 A | 2/1991 | Pocknell |
| 4,991,640 A | 2/1991 | Verkindt et al. |
| 5,002,045 A | 3/1991 | Spademan |
| 5,005,527 A | 4/1991 | Hatfield |
| 5,005,627 A | 4/1991 | Hatfield |
| 5,016,621 A | 5/1991 | Bender |
| 5,018,514 A | 5/1991 | Grood et al. |
| 5,020,196 A | 6/1991 | Panach et al. |
| 5,022,109 A | 6/1991 | Pekar |
| 5,036,837 A | 8/1991 | Mitchell et al. |
| 5,063,916 A | 11/1991 | France et al. |
| 5,067,772 A | 11/1991 | Koa |
| 5,077,870 A | 1/1992 | Melbye et al. |
| 5,085,210 A | 2/1992 | Smith, III |
| 5,112,296 A | 5/1992 | Beard et al. |
| 5,139,477 A | 8/1992 | Peters |
| 5,152,038 A | 10/1992 | Schoch |
| 5,154,682 A | 10/1992 | Kellerman |
| 5,157,813 A | 10/1992 | Carroll |
| 5,181,331 A | 1/1993 | Berger |
| 5,227,698 A | 7/1993 | Simpson |
| 5,242,379 A | 9/1993 | Harris et al. |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,306,230 A | 4/1994 | Bodine |
| 5,314,455 A | 5/1994 | Johnson, Jr. et al. |
| 5,316,547 A | 5/1994 | Gildersleeve |
| 5,322,729 A | 6/1994 | Heeter et al. |
| 5,334,135 A | 8/1994 | Grim et al. |
| 5,344,135 A | 9/1994 | Isobe et al. |
| 5,368,549 A | 11/1994 | McVicker |

(56) References Cited

U.S. PATENT DOCUMENTS

| | | |
|---|---|---|
| 5,383,845 A | 1/1995 | Nebolon |
| 5,385,538 A | 1/1995 | Mann |
| 5,397,296 A | 3/1995 | Sydor et al. |
| 5,415,625 A | 5/1995 | Cassford |
| 5,431,623 A | 7/1995 | Rice |
| 5,437,619 A | 8/1995 | Malewicz et al. |
| 5,445,602 A | 8/1995 | Grim et al. |
| 5,449,341 A | 9/1995 | Harris |
| 5,458,565 A | 10/1995 | Tillinghast, III et al. |
| 5,468,219 A | 11/1995 | Crippen |
| 5,472,413 A | 12/1995 | Detty |
| 5,474,524 A | 12/1995 | Carey |
| 5,497,513 A | 3/1996 | Arabeyre et al. |
| 5,500,268 A | 3/1996 | Billarant |
| 5,512,039 A | 4/1996 | White |
| 5,513,658 A | 5/1996 | Goseki |
| 5,514,081 A | 5/1996 | Mann |
| 5,520,622 A | 5/1996 | Bastyr et al. |
| 5,527,269 A | 6/1996 | Reithofer |
| 5,538,488 A | 7/1996 | Villepigue |
| 5,540,982 A | 7/1996 | Scholz et al. |
| 5,542,911 A | 8/1996 | Cassford et al. |
| 5,562,605 A | 10/1996 | Taylor |
| 5,599,288 A | 2/1997 | Shirley et al. |
| 5,695,452 A | 2/1997 | Grim et al. |
| 5,614,045 A | 3/1997 | Billarant |
| 5,624,389 A | 4/1997 | Zepf |
| 5,635,201 A | 6/1997 | Fabo |
| 5,638,588 A | 6/1997 | Jungkind |
| 5,654,070 A | 8/1997 | Billarant |
| 5,656,226 A | 8/1997 | McVicker |
| 5,665,449 A | 9/1997 | Billarant |
| 5,681,271 A | 10/1997 | Nelson |
| 5,685,830 A | 11/1997 | Bonutti |
| 5,711,029 A | 1/1998 | Visco et al. |
| 5,713,837 A | 2/1998 | Grim et al. |
| D392,877 S | 3/1998 | Eguchi |
| 5,728,057 A | 3/1998 | Ouellette et al. |
| 5,728,058 A | 3/1998 | Ouellette et al. |
| 5,730,710 A | 3/1998 | Eichhorn et al. |
| 5,737,854 A | 4/1998 | Sussmann |
| 5,759,167 A | 6/1998 | Shields, Jr. et al. |
| 5,769,808 A | 6/1998 | Matthijs et al. |
| 5,769,809 A | 6/1998 | Witzel |
| 5,774,902 A | 7/1998 | Gehse |
| 5,795,640 A | 8/1998 | Billarant |
| 5,807,294 A | 9/1998 | Cawley et al. |
| 5,823,931 A | 10/1998 | Gilmour |
| 5,823,981 A | 10/1998 | Grim et al. |
| 5,840,398 A | 11/1998 | Billarant |
| 5,857,988 A | 1/1999 | Shirley |
| 5,857,989 A | 1/1999 | Smith, III |
| 5,865,776 A | 2/1999 | Springs |
| 5,865,777 A | 2/1999 | Detty |
| 5,865,782 A | 2/1999 | Fareed |
| 5,873,848 A | 2/1999 | Fulkerson |
| 5,891,061 A | 4/1999 | Kaiser |
| 5,891,071 A | 4/1999 | Stearns et al. |
| 5,900,303 A | 5/1999 | Billarant |
| 5,916,187 A | 6/1999 | Brill |
| 5,948,707 A | 9/1999 | Crawley et al. |
| 5,971,946 A | 10/1999 | Quinn |
| 6,010,474 A | 1/2000 | Wycoki |
| 6,021,780 A | 2/2000 | Darby |
| 6,022,617 A | 2/2000 | Calkins |
| 6,024,712 A | 2/2000 | Iglesias et al. |
| D422,709 S | 4/2000 | Caswell |
| 6,059,834 A * | 5/2000 | Springs ............... A61F 2/7812 623/32 |
| 6,063,048 A | 5/2000 | Bodenschatz et al. |
| 6,110,138 A | 8/2000 | Shirley |
| 6,111,138 A | 8/2000 | Van Wijck et al. |
| 6,129,695 A | 10/2000 | Peters et al. |
| 6,142,965 A | 11/2000 | Mathewson |
| 6,149,616 A | 11/2000 | Szlema et al. |
| 6,149,690 A | 11/2000 | Belzidsky |
| 6,152,893 A | 11/2000 | Pigg et al. |
| D435,145 S | 12/2000 | Lindsey |
| 6,159,583 A | 12/2000 | Calkins |
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,371,933 B1 | 4/2002 | Gardon-Mollard |
| D457,293 S | 5/2002 | Maurer |
| 6,402,713 B1 | 6/2002 | Doyle |
| 6,405,731 B1 | 6/2002 | Ching |
| 6,408,445 B1 | 6/2002 | Matthews |
| 6,412,311 B1 | 7/2002 | Nakai |
| 6,413,232 B1 | 7/2002 | Townsend et al. |
| 6,416,074 B1 | 7/2002 | Maravetz et al. |
| 6,430,970 B1 | 8/2002 | Gardon-Mollard et al. |
| 6,440,526 B1 | 8/2002 | Gamble et al. |
| 6,461,318 B2 | 10/2002 | Freeman et al. |
| 6,485,776 B2 | 11/2002 | Janusson et al. |
| 6,520,926 B2 | 2/2003 | Hall |
| 6,523,729 B1 | 2/2003 | Gardon-Mollard |
| 6,540,703 B1 | 4/2003 | Lerman |
| 6,540,709 B1 | 4/2003 | Smits |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,543,158 B2 | 8/2003 | Dieckhaus |
| 6,634,190 B2 | 10/2003 | Didier-Laurent |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 | 5/2004 | Iverson et al. |
| 6,740,054 B2 | 5/2004 | Stearns |
| D492,787 S | 7/2004 | Weaver, II et al. |
| 6,769,155 B2 | 8/2004 | Hess et al. |
| 6,773,411 B2 | 8/2004 | Alvarez |
| 6,838,402 B2 | 1/2005 | Harris et al. |
| 6,861,371 B2 | 3/2005 | Kamikawa et al. |
| 6,861,379 B1 | 3/2005 | Blaszcykiewicz |
| 6,898,804 B2 | 5/2005 | Sandler |
| 6,898,826 B2 | 5/2005 | Draper et al. |
| 6,936,020 B2 | 8/2005 | Davis |
| 7,017,376 B2 | 3/2006 | Meckley et al. |
| D519,637 S | 4/2006 | Nordt et al. |
| D519,638 S | 4/2006 | Nordt et al. |
| 7,025,738 B2 | 4/2006 | Hall |
| D520,141 S | 5/2006 | Nordt et al. |
| D521,644 S | 5/2006 | Nordt et al. |
| 7,037,287 B2 | 5/2006 | Cormier et al. |
| 7,076,973 B1 | 7/2006 | Chesebro, Jr. et al. |
| 7,083,586 B2 | 8/2006 | Simmons et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,201,728 B2 | 4/2007 | Sterling |
| 7,273,464 B2 | 9/2007 | Reinhardt |
| D555,339 S | 11/2007 | Chang |
| 7,303,539 B2 | 12/2007 | Binder et al. |
| 7,367,958 B2 | 5/2008 | McBean et al. |
| D572,827 S | 7/2008 | Reinhardt et al. |
| D574,084 S | 7/2008 | Reinhardt |
| 7,448,115 B2 | 11/2008 | Howell et al. |
| 7,473,236 B1 | 1/2009 | Mathewson |
| 7,517,331 B2 | 4/2009 | Reinhardt et al. |
| D601,705 S | 10/2009 | Bauerfeind et al. |
| 7,597,675 B2 | 10/2009 | Ingimundarson et al. |
| 7,625,350 B2 | 12/2009 | Hunter et al. |
| 7,625,625 B2 | 12/2009 | Rios et al. |
| 7,698,909 B2 | 4/2010 | Hannula et al. |
| 7,699,195 B2 | 4/2010 | Scott |

(56) References Cited

U.S. PATENT DOCUMENTS

| | | |
|---|---|---|
| 7,713,225 B2 | 5/2010 | Ingimundarson et al. |
| 7,749,181 B2 | 7/2010 | Simmons et al. |
| 7,749,183 B2 | 7/2010 | Ingimundarson et al. |
| 7,762,973 B2 | 7/2010 | Einarsson et al. |
| 7,794,418 B2 | 9/2010 | Ingimundarson et al. |
| D626,241 S | 10/2010 | Sagnip et al. |
| 7,806,842 B2 | 10/2010 | Stevenson et al. |
| 7,819,830 B2 | 10/2010 | Sindel et al. |
| D629,115 S | 12/2010 | Robertson |
| D630,333 S | 1/2011 | Chiang |
| 7,867,183 B2 | 1/2011 | Kazmierczak et al. |
| 7,871,388 B2 | 1/2011 | Brown |
| 7,874,996 B2 | 1/2011 | Weinstein et al. |
| D635,266 S | 3/2011 | Chiang |
| D635,267 S | 3/2011 | Chiang |
| 7,896,827 B2 | 3/2011 | Ingimundarson et al. |
| 7,905,851 B1 | 3/2011 | Bledsoe |
| 7,937,973 B2 | 5/2011 | Sorensen et al. |
| 7,943,219 B2 | 5/2011 | Krueger |
| 7,959,590 B2 | 6/2011 | Scott |
| 8,016,781 B2 | 9/2011 | Ingimundarson et al. |
| 8,025,632 B2 | 9/2011 | Einarsson |
| 8,043,242 B2 | 10/2011 | McSpadden et al. |
| 8,043,244 B2 | 10/2011 | Einarsson et al. |
| 8,048,014 B2 | 11/2011 | Brown |
| 8,066,654 B2 | 11/2011 | Sandifer et al. |
| D654,182 S | 2/2012 | Chiang |
| 8,118,765 B2 | 2/2012 | Magnusson |
| D657,063 S | 4/2012 | Chiang |
| 8,216,170 B2 | 7/2012 | Ingimundarson et al. |
| D665,950 S | 8/2012 | Rokitta |
| 8,241,234 B2 | 8/2012 | Ingimundarson et al. |
| 8,257,293 B2 | 9/2012 | Ingimundarson et al. |
| 8,267,879 B2 | 9/2012 | Ingimundarson et al. |
| 8,277,401 B2 | 10/2012 | Hammerslag et al. |
| 8,302,269 B2 | 11/2012 | Pitman |
| 8,328,746 B2 | 12/2012 | Ingimundarson et al. |
| 8,328,747 B2 | 12/2012 | Matsunaga |
| 8,425,441 B2 | 4/2013 | Ingimundarson |
| D683,118 S | 5/2013 | Pauk |
| 8,556,783 B1 | 10/2013 | Ihli et al. |
| 8,585,623 B2 | 11/2013 | Ingimundarson |
| 8,745,829 B2 | 6/2014 | Wanzenboeck et al. |
| 8,864,692 B2 | 10/2014 | Ingimundarson et al. |
| 8,950,013 B2 | 2/2015 | Bates |
| 9,066,546 B2 | 6/2015 | Getzwiller |
| 9,113,998 B2 | 8/2015 | Romo |
| D741,622 S | 10/2015 | Jensen et al. |
| 9,173,763 B2 | 11/2015 | Gilmer et al. |
| 9,220,622 B2 | 12/2015 | Ingimundarson et al. |
| 9,265,644 B2 | 2/2016 | Einarsson et al. |
| 9,265,645 B2 | 2/2016 | Ingimundarson et al. |
| D759,826 S | 6/2016 | Martinez et al. |
| 9,358,146 B2 | 6/2016 | Thorsteinsdottir et al. |
| 9,364,365 B2 | 6/2016 | Omarsson et al. |
| 9,375,341 B2 | 6/2016 | Ingimundarson et al. |
| 9,393,147 B2 | 7/2016 | Scheuermann et al. |
| 9,474,334 B2 | 10/2016 | Jonsson et al. |
| 9,498,025 B2 | 11/2016 | Omarsson et al. |
| D777,468 S | 1/2017 | Currier |
| 9,545,328 B2 | 1/2017 | Hess et al. |
| D778,563 S | 2/2017 | Kanata |
| D783,207 S | 4/2017 | Lindsey |
| D783,970 S | 4/2017 | Kanata |
| D788,540 S | 6/2017 | Mock |
| D789,547 S | 6/2017 | Matfus et al. |
| D794,932 S | 8/2017 | Parrett et al. |
| D796,809 S | 9/2017 | Williams, Jr. |
| D804,043 S | 11/2017 | Gildersleeve |
| 9,814,615 B2 | 11/2017 | Ingimundarson |
| D812,236 S | 3/2018 | Burke et al. |
| D816,234 S | 4/2018 | Calvello et al. |
| D831,221 S | 10/2018 | Smith |
| 10,123,889 B2 | 11/2018 | Egilsson et al. |
| 10,159,592 B2 | 12/2018 | Ingimundarson et al. |
| 10,165,803 B2 | 1/2019 | Hoeven |
| D843,684 S | 3/2019 | Hamilton et al. |
| 10,758,393 B2 | 9/2020 | Ingimundarson et al. |
| 10,966,851 B2 | 4/2021 | Ingimundarson et al. |
| 11,872,150 B2 * | 1/2024 | Sigurdsson ............ A61F 5/0123 |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0107464 A1 | 8/2002 | Castillo |
| 2002/0132086 A1 | 9/2002 | Su-Tuan |
| 2003/0032907 A1 | 2/2003 | Prahl |
| 2003/0069531 A1 | 4/2003 | Hall |
| 2003/0114782 A1 | 6/2003 | Chiang et al. |
| 2003/0204156 A1 | 10/2003 | Nelson et al. |
| 2003/0216676 A1 | 11/2003 | Gardon-Mollard |
| 2004/0002674 A1 | 1/2004 | Sterling |
| 2004/0054311 A1 | 2/2004 | Sterling |
| 2004/0058102 A1 | 3/2004 | Baychar |
| 2004/0137178 A1 | 7/2004 | Janusson et al. |
| 2004/0137192 A1 | 7/2004 | McVicker |
| 2004/0153016 A1 | 8/2004 | Salmon et al. |
| 2004/0153017 A1 | 8/2004 | Simmons et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0020951 A1 | 1/2005 | Gaylord et al. |
| 2005/0038367 A1 | 2/2005 | McCormick et al. |
| 2005/0081339 A1 | 4/2005 | Sakabayashi |
| 2005/0159691 A1 | 7/2005 | Turrini et al. |
| 2005/0160627 A1 | 7/2005 | Dalgaard et al. |
| 2005/0273025 A1 | 12/2005 | Houser |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verkade et al. |
| 2006/0090806 A1 | 5/2006 | Friedline et al. |
| 2006/0094999 A1 | 5/2006 | Cropper |
| 2006/0116619 A1 | 6/2006 | Weinstein et al. |
| 2006/0135900 A1 | 6/2006 | Ingimundarson et al. |
| 2006/0135902 A1 | 6/2006 | Ingimundarson et al. |
| 2006/0135903 A1 | 6/2006 | Ingimundarson et al. |
| 2006/0151550 A1 | 7/2006 | Chevalier |
| 2006/0155229 A1 | 7/2006 | Ceriani et al. |
| 2006/0156517 A1 | 7/2006 | Hammerslag et al. |
| 2006/0191110 A1 | 8/2006 | Howell et al. |
| 2006/0246802 A1 | 11/2006 | Hughes et al. |
| 2007/0060853 A1 | 3/2007 | Sindel et al. |
| 2007/0083136 A1 | 4/2007 | Einarsson |
| 2007/0106191 A1 | 5/2007 | Mueller et al. |
| 2007/0130665 A1 | 6/2007 | Wang |
| 2007/0148409 A1 | 6/2007 | Rios et al. |
| 2007/0167892 A1 | 7/2007 | Gramza et al. |
| 2007/0167895 A1 | 7/2007 | Gramza et al. |
| 2007/0185425 A1 | 8/2007 | Einarsson et al. |
| 2007/0197944 A1 | 8/2007 | Bruce et al. |
| 2007/0225824 A1 | 9/2007 | Einarsson |
| 2008/0034459 A1 | 2/2008 | Nordt, III et al. |
| 2008/0066272 A1 | 3/2008 | Hammerslag et al. |
| 2008/0139982 A1 | 6/2008 | Magnusson |
| 2008/0195014 A1 | 8/2008 | Ingimundarson et al. |
| 2008/0208095 A1 | 8/2008 | Kazmierczak et al. |
| 2008/0229556 A1 | 9/2008 | Hammer |
| 2008/0294079 A1 | 11/2008 | Sterling et al. |
| 2009/0099562 A1 | 4/2009 | Ingimundarson et al. |
| 2009/0126413 A1 | 5/2009 | Sorensen et al. |
| 2009/0156973 A1 | 6/2009 | Scott |

(56) References Cited

U.S. PATENT DOCUMENTS

| | | |
|---|---|---|
| 2009/0259154 A1 | 10/2009 | Nace |
| 2010/0036303 A1 | 2/2010 | Bauerfeind et al. |
| 2010/0068464 A1 | 3/2010 | Meyer |
| 2010/0125231 A1 | 5/2010 | Knecht |
| 2010/0152635 A1 | 6/2010 | Borden |
| 2011/0057466 A1 | 3/2011 | Sachee et al. |
| 2011/0172582 A1 | 7/2011 | Darian |
| 2011/0275970 A1 | 11/2011 | Paulos et al. |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2012/0141750 A1 | 6/2012 | Taylor |
| 2012/0165713 A1 | 6/2012 | Forbes et al. |
| 2012/0220910 A1 | 8/2012 | Gaylord et al. |
| 2012/0232448 A1 | 9/2012 | Wüst |
| 2012/0277649 A1 | 11/2012 | Matsuo et al. |
| 2013/0022794 A1 | 1/2013 | Ng et al. |
| 2013/0053743 A1 | 2/2013 | Reinhardt et al. |
| 2013/0053744 A1 | 2/2013 | Convert et al. |
| 2013/0110023 A1 | 5/2013 | Scheuermann et al. |
| 2013/0116609 A1 | 5/2013 | Matsuo et al. |
| 2013/0184628 A1 | 7/2013 | Ingimundarson et al. |
| 2013/0211304 A1 | 8/2013 | Romo et al. |
| 2013/0245523 A1 | 9/2013 | Romo |
| 2013/0251962 A1 | 9/2013 | Reid, Jr. |
| 2013/0312294 A1 | 11/2013 | Tang |
| 2013/0333706 A1 | 12/2013 | Bauerfeind |
| 2014/0079900 A1 | 3/2014 | Ramirez |
| 2014/0121579 A1 | 5/2014 | Hinds |
| 2014/0137314 A1 | 5/2014 | Needham |
| 2014/0194801 A1 | 7/2014 | Ingimundarson et al. |
| 2014/0213947 A1 | 7/2014 | Omarsson et al. |
| 2014/0214016 A1 | 7/2014 | Ingimundarson et al. |
| 2014/0257158 A1 | 9/2014 | Lee et al. |
| 2014/0303534 A1 | 10/2014 | Huffa et al. |
| 2015/0032041 A1 | 1/2015 | Ingimundarson et al. |
| 2015/0038891 A1 | 2/2015 | Lipton et al. |
| 2015/0121657 A1 | 5/2015 | Ingimundarson et al. |
| 2015/0272767 A1 | 10/2015 | Field |
| 2015/0290014 A1 | 10/2015 | Anglada et al. |
| 2016/0081835 A1 | 3/2016 | Grange et al. |
| 2016/0193066 A1 | 7/2016 | Albertsson et al. |
| 2016/0242945 A1 | 8/2016 | Thorsetinsdottir et al. |
| 2016/0278959 A1 | 9/2016 | Omarsson et al. |
| 2016/0296360 A1 | 10/2016 | Ingimundarson et al. |
| 2017/0007435 A1 | 1/2017 | Klutts |
| 2017/0020707 A1 | 1/2017 | Duport et al. |
| 2017/0027719 A1 | 2/2017 | Bache et al. |
| 2017/0065037 A1 | 3/2017 | Omarsson et al. |
| 2017/0119568 A1 | 5/2017 | Chiang et al. |
| 2017/0348130 A1 | 12/2017 | Petursson |
| 2017/0348131 A1 | 12/2017 | Petursson |
| 2018/0042754 A1* | 2/2018 | Ingimundarson ..... A61F 5/0109 |
| 2018/0078398 A1 | 3/2018 | Ingimundarson et al. |
| 2019/0037937 A1 | 2/2019 | Ito et al. |
| 2019/0091055 A1 | 3/2019 | Best et al. |
| 2019/0105189 A1 | 4/2019 | Petursson et al. |
| 2019/0314542 A1 | 10/2019 | Ish Cassit |

FOREIGN PATENT DOCUMENTS

| | | |
|---|---|---|
| CN | 101128169 A | 2/2008 |
| CN | 101278011 B | 10/2012 |
| DE | 846895 C | 8/1952 |
| DE | 100 04 561 A1 | 8/2001 |
| DE | 20 2004 012 892 U1 | 10/2004 |
| DE | 102010019405 A1 | 8/2011 |
| EP | 0050769 A1 | 5/1985 |
| EP | 0 196 204 A2 | 10/1986 |
| EP | 0 611 069 A | 8/1994 |
| EP | 1016351 A1 | 7/2000 |
| EP | 2283795 A1 | 2/2011 |
| EP | 2612624 A1 | 7/2013 |
| EP | 2612626 A2 | 7/2013 |
| EP | 2536370 B1 | 1/2015 |
| EP | 2124849 B1 | 4/2015 |
| FR | 2399811 A1 | 3/1979 |
| FR | 2553996 A1 | 5/1985 |
| FR | 2 766 359 A1 | 1/1999 |
| FR | 2775431 A1 | 9/1999 |
| FR | 2807644 A1 | 10/2001 |
| FR | 2879405 A1 | 6/2006 |
| GB | 1209413 A | 10/1970 |
| GB | 2136294 A | 9/1984 |
| GB | 2 455 972 A | 7/2009 |
| JP | H1056932 A | 3/1998 |
| KR | 20190051232 A | 5/2019 |
| WO | 88/01855 A1 | 3/1988 |
| WO | 9105498 A1 | 5/1991 |
| WO | 94/00082 A1 | 1/1994 |
| WO | 9944548 A1 | 9/1999 |
| WO | 00/49982 A1 | 8/2000 |
| WO | 00/70984 A1 | 11/2000 |
| WO | 03096851 A1 | 11/2003 |
| WO | 2006/015599 A1 | 2/2006 |
| WO | 2006/069221 A2 | 6/2006 |
| WO | 2006/069222 A2 | 6/2006 |
| WO | 2008006142 A1 | 1/2008 |
| WO | 2008/115376 A1 | 9/2008 |
| WO | 2009052031 A1 | 4/2009 |
| WO | 2010/117749 A2 | 10/2010 |
| WO | 2011073803 A2 | 6/2011 |
| WO | 2012003992 A1 | 1/2012 |
| WO | 2012051385 A1 | 4/2012 |
| WO | 2017019485 A1 | 2/2017 |
| WO | 2017135473 A1 | 8/2017 |
| WO | 2018031618 A1 | 2/2018 |
| WO | 2019104263 A1 | 5/2019 |

OTHER PUBLICATIONS

International Search Report from PCT Application No. PCT/US2017/036073, Nov. 22, 2017.
International Search Report from PCT Application No. PCT/US2018/054820, Feb. 8, 2019.
Article: "An Orthosis for Medial or Lateral Stabilization of Arthritic Knees", by S. Cousins and James Foort, Orthotics and Prosthetics, vol. 29, No. 4, pp. 21-26, Dec. 1975.
Advertising Brochure: "NUKO Camp", 6 pages, Camp International, Inc. Jackson, MI (1984).
Advertising Brochure: "Lerman Multi-Ligaments Knee Control Orthosis", 2 pages, Zinco Industries, Inc. of Montrose, CA (1985).
"Information on Flexible Polyurethane Foam", In Touch, vol. 4, No. 3, Jul. 1994, 5 pages.
Advertisement: "Custom Engineered Fabrics and Products for Advanced High Performance", 1 page, Gehring Textiles (visited Dec. 15, 2005), http://www.gehringtextiles.com/d3.html.
Article: "Osteoarthritis of the Knee: An Information Booklet", Arthritis Research Campaign (visited Dec. 14, 2004) http://www.arc.org.uk/about_arth/booklets/6027/6027.htm.
Advertising Brochure: "Freedom to Perform-Fusion", 5 pages, (2005).
Advertising Brochure: "Fusion", 6 pages, Breg, Inc. of Vista, CA (2005).
Advertising Brochure: "Fusion XT", 2 pages, Breg, Inc. of Vista, CA (2005).
Advertising Brochure: "Anderson Knee Stabler", 4 pages, Omni Scientific, Inc. of Lafayette, CA. Feb. 7, 2013.
Advertising Brochure: "OTI Brace", 4 pages, Orthopedic Technology, Inc. of San Leandro, CA. Feb. 7, 2013.
Advertising Brochure: "The Four Axioms of Functional Bracing", 2 pages, Bledsoe by Medical Technology, Inc. (2005).
Advertising Brochure: "The Leader in Knee Motion Management," 8 pages. Donjoy, Carsbad, CA. Feb. 7, 2013.
Advertising Brochure: "The Lenox Hill Lightweight", 1page, Lenox Hill Brace, Inc., New York, NY. Feb. 7, 2013.
Advertising Brochure: "XCL System", 2 pages, Innovation Sports of Foothill Ranch, CA. Feb. 7, 2013.

(56) References Cited

OTHER PUBLICATIONS

Advertising Brochure: "The 9 Innovations of the Axiom Custom Brace", 1 page, Bledsoe, Medical Technology, Inc. (2005).
Technical Manual: Bellacure: Restore Your Lifestyle, 10 pages, Bellacure, Inc. (2005).
Technical Manual: "Boa Technology", 3 pages, Boa Technology, Inc. of Steamboat Springs, CO, Feb. 7, 2013.
Advertising Brochure: "GII Unloader Select", 2 pagse, Ossur HF of Reykjavik, Iceland (visited Mar. 8, 2005), http://www.ossur.com/pring.asp?pageID=1729.
Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.
Advertisement: "Triax", 1 page, Lanxess AG (visited Mar. 8, 2005), http://www.techcenter.lanxess.com/sty/emea/en/products/description/57/index/jsp?print=true&pid=57.
Reference: "Anatomical Planes", 1 page, (visited Mar. 26, 2005), http://www.spineuniverse.com/displayarticle.phpo/article1023.html.
Advertisement: "M2 Inc. Parts Catalog", 3 pages, M2 Inc. of Winooski, VT (visited Mar. 29, 2005), http://www.m2intl.com/medical.MedClsr.htm.
Advertisement: "Axiom", 3 pages, Bledsoe by Medical Technology, Inc. (visited Jun. 15, 2005), http://www.bledsoebrace.com/custom/axiom.asp.
Advertisement: "Bellacure: The Treatment Device", 6 pages, Bellacure, Inc. (visited Jan. 5, 2006), http://www.bellacure.com/products/index/html.
Advertisement: "Lerman 3-Point Knee Orthosis", 2 pages, Becker Orthopedic of Troy, MI (visited Feb. 26, 2006), http://www.beckerortho.com/knee/3-point/htm.
Article: "Thermoplastic Elastomers TPE, TPR, TPV", 6 pages (visited Mar. 14, 2007), http://www.bpf.co.uk.bpfindustry/plastics_thermplasrubber_TBR.cfm.
International Search Report from PCT Application No. PCT/US2021/064789, Apr. 7, 2022.
Product Information, "BORT AsymmetricPlus, No. 114900, Unit PCE", downloaded Mar. 31, 2014, 3 pages. Retrieved at http://shop.bort.de/en/produkt-details.aspx?ProductNo=114900.
Product Information, "BORT AsymmetricPlus, No. 114700, Unit PCE", downloaded Mar. 31, 2014, 3 pages. Retrieved at http://shop.bort.de/en/produkt-details.aspx?ProductNo=114700.
Brochure, "BORT Asymmetric Plus, Die Mehrwert-Orthese bei Patella-Luxation", downloaded Aug. 2012. 16 pages. Retrieved at http://www.bort.com.
Catalog, "Bracing and Supports Catalog," Ottobock, 2015, pp. 1-100.
Catalog, "Continuum of Care for Orthopedic Clinics," BSNmedical, 2016, pp. 1-48.
Catalog, "Product Guide," Mueller Sports Medicine, 2016, pp. 1-92.
Catalog, "Aircast Procare Exos Product Catalog," DJO Global, 2014, pp. 1-144.
Brochure, "Action Reliever Active Pain Relief For Knee Osteoarthritis," Thuasne, 2017, 2 Pages.
Catalog, "Catalogue 2017," Bort Medical, 2017, pp. 1-196.
Catalog, "2017 International Product Catalog," BREG, 2017, pp. 1-100.
Catalog, "International Catalogue," Gibaud, Jun. 2014, pp. 1-92.
Product Information, "GenuForce," DJO Global, retrieved from www.djoglobal.com/products/donjoy/genuforce, downloaded Nov. 9, 2017, 3 Pages.
Product Information, "Genumedi & Genumedi Extra Wide," Medi, retrieved from https://mediusa.com/portfolio-item/genumedi/, downloaded Nov. 9, 2017, 5 Pages.
Product Information, "Genumedi pro," Medi, retrieved from http://mediusa.com/portfolio-item/genumedi-pro/, downloaded Nov. 9, 2017, 5 Pages.
Product Information, "Genumedi PT," Medi, retrieved from http://mediusa.com/portfolio-item/genumedi-pt/, downloaded Nov. 9, 2017, 5 Pages.
Product Information, "GenuTrain P3," Bauerfeind, downloaded Nov. 9, 2017, 3 Pages.
Product Information, "Lumbamed Basic," Medi, retrieved from http://mediusa.com/portfolio-item/lumbamed-basic/, downloaded Nov. 9, 2017, 5 Pages.
Product Information, "Lumbamed Plus," Medi, retrieved from http://mediusa.com/portfolio-item/lumbamed-plus/, downloaded Nov. 9, 2017, 7 Pages.
Product Information, "LumboTrain," Bauerfeind, downloaded Nov. 9, 2017, 3 Pages.
Product Information, "LumboTrain Lady," Bauerfeind, downloaded Nov. 9, 2017, 3 Pages.
Product Information, "MalleoTrain," Bauerfeind, downloaded Nov. 9, 2017, 3 Pages.
Catalog, "OA & Injury Solutions Catalogue," OSSUR, 2017, pp. 1-121.
Catalog, "Product Catalog Supports and Orthoses," Bauerfeind, 2015, pp. 1-72.
Catalog, "Push For Freedom," Push Braces, downloaded Nov. 9, 2017, pp. 1-28.
Product Information, "Sports Ankle Support Dynamic," Bauerfeind, downloaded Nov. 9, 2017, 2 Pages.
Product Information, "Sports Back Support," Bauerfeind, downloaded Nov. 9, 2017, 3 Pages.
Product Information, "Sports Elbow Support," Bauerfeind, downloaded Nov. 9, 2017, 4 Pages.
Product Information, "Sports Knee Support," Bauerfeind, downloaded Nov. 9, 2017, 3 Pages.
Catalog, "Orthopedic Products 2016," Thuasne, 2016, pp. 1-32.
International Search Report from PCT Application No. PCT/US2017/046028, Nov. 7, 2017.
International Search Report and Written Opinion from PCT Application No. PCT/US2018/062420, Mar. 14, 2019.
"Choose Dow silicone PSA for high performance," published in 2019 by the Dow Chemical Company, 12 Pages.

* cited by examiner

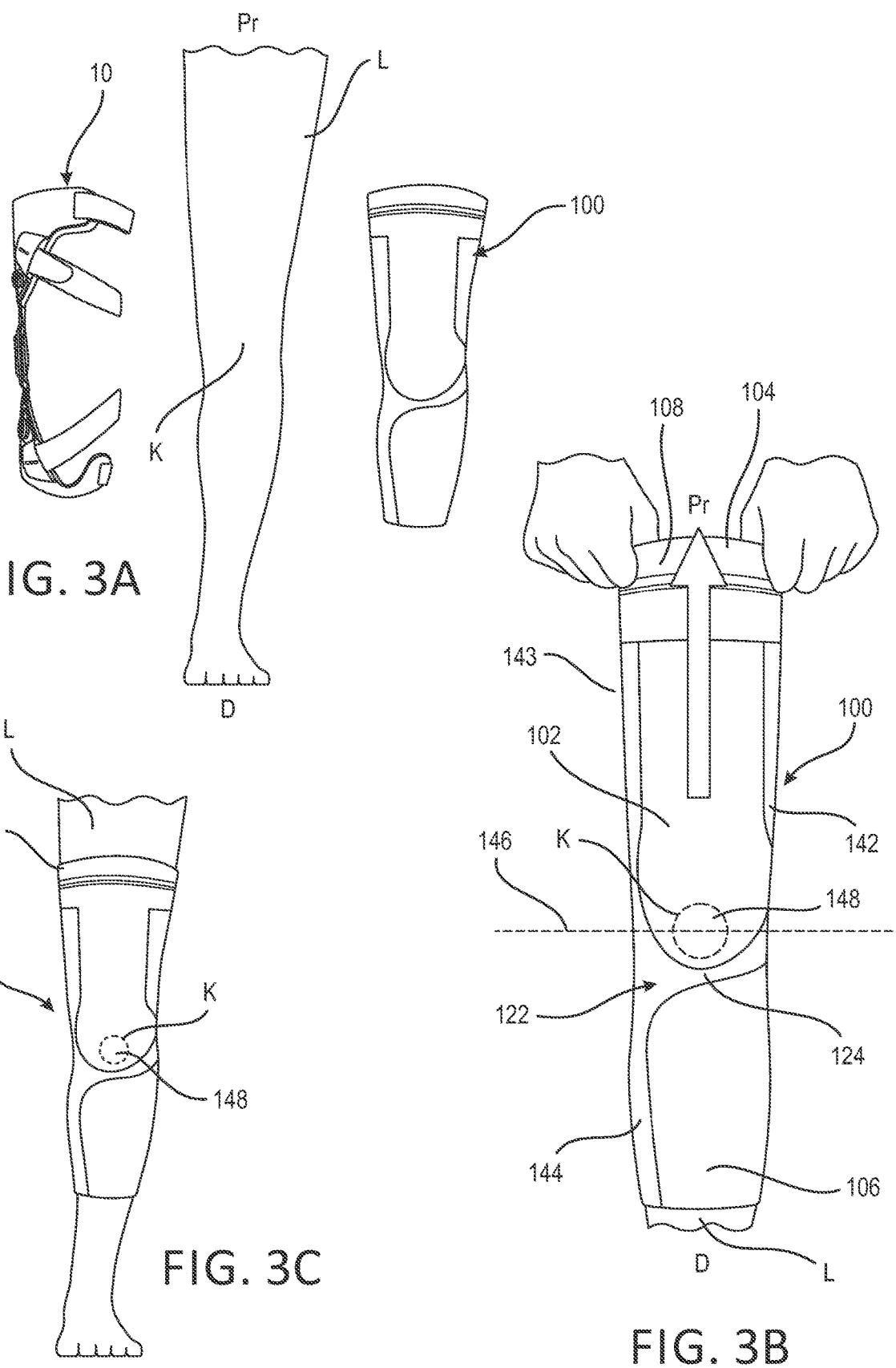

SLEEVE AND METHOD FOR USE WITH ORTHOPEDIC DEVICE

FIELD OF ART

The embodiments of this disclosure are directed to a sleeve for use with an orthopedic device. The sleeve is arranged for intimately fitting to, supporting, and guiding anatomical segments or joints with an orthopedic device placed thereover.

BACKGROUND

Orthopedic braces and supports are arranged to restrict, inhibit, immobilize, or otherwise control motion about the human body's anatomical segments or joints. These braces and supports provide compression, support, and stability. Many known braces and supports incorporate rigid members and hinges for immobilizing a joint or facilitating movement of the joint. Orthopedic bracing has tended toward greater rigidity to provide ultimate immobilization with a reduced margin of error in mobility.

There tends to be an inverse relationship between the rigidity of the device and user comfort/compliance. The more rigid the device is, the less likely it will be worn, especially over extended periods. Users may find wearing such an orthopedic device uncomfortable despite the padding offered by a rigid orthopedic device. The user may have skin irritation and migration of the orthopedic device over the user's skin. If the user removes a required device to increase comfort, rehabilitation may be hampered, and the risk of further injury may be elevated.

Flexible braces and supports exist which offer compression, support, and stability. However, many are formed from synthetic materials, such as Neoprene, and lack sufficient structural features to significantly offer bracing and corrective treatment (i.e., osteoarthritis bracing). These types of braces can give rise to allergic reactions and get hot. In addition, because they typically rely on a sheet of homogeneous material, they lack areas having different properties and may be ill-fitting or ineffective as a joint requires different areas of compression.

Flexible orthopedic devices and sleeves provide anatomical fit by conforming to a user's anatomy for physiologically correct support. They are flexible and arranged for contouring to a body or joint to minimize movement restriction and discomfort. The devices may be configured to stretch in different ways to enable greater muscle stability. Because of their sizing and fit, these devices support and improve circulation and reduce pain and inflammation. Other types of flexible orthopedic devices and/or sleeves may include Neoprene and/or other textiles and materials, and may include other tubular configurations or other shapes and configurations.

Unfortunately, known flexible orthopedic devices and sleeves often lack adequate strapping and instead rely on their elasticity for being maintained on a limb and/or preventing unwanted device migration from an intended fit. These devices may be limited to uniform elasticity, whereas the user may require different degrees of elasticity depending on where the device is intended to be placed over the anatomy, for different types of recoveries from different types of pathologies, and/or for being retained on the user and treatment of specific anatomy. As a result, such devices may not provide sufficient support, and offer more proprioceptive than functional capabilities.

Given many orthopedic devices' tubular nature, including flexible orthopedic devices or sleeves, an issue often arises with migration control. Taking for instance, a knee support, as the leg is conical, it is difficult to control the migration of the knee support during repeated movement between flexion and extension. Often straps are used to hold the support on the leg, or light frictional material is applied to the support's interior. Unfortunately, the straps may exert too much compressive force on the leg, creating discomfort and impeding the user's activities.

The frictional material that serves to hold the orthopedic device in place must have low frictional qualities to allow the user to slide the support on the leg, which has the undesired effect of reducing the effectiveness of anti-migration means and control. Compensating for the use of low friction materials with a more highly compressive body panel to better hold the device in place also creates problems, as highly compressive body panels are extremely difficult to don. When donned, they are uncomfortable for a user and are thus not suitable for extended use. These current means for migration control require improvement to balance and optimize migration control, ease of use, and donning and doffing the support.

Strap designs in existing devices mistake the proper placement of straps and thus do not offer optimal support for pathologies such as osteoarthritis users. Many orthopedic devices feature straps connected at a crossing or intersecting point on the orthopedic device, usually directly at and over the hinge located on the device's medial or lateral side. However, this is not an ideal placement of the intersection of the straps, as it does not effectively unload the knee and thus does not effectively treat the underlying condition, such as osteoarthritis. Straps may also be difficult to apply and adjust repeatedly. In addition, straps may stray from their intended location on the brace, reducing their effectiveness. Straps may also get tangled with each other or be damaged by external forces.

Another issue in orthopedic devices is the difficulty in donning and doffing due to a user's poor grip on the device. Directly gripping the tubular body can lead to undesired stretching and damage to the device while also being difficult for a user. Certain orthopedic devices allow for a tab that guides a strap on an outside surface of the device to serve additionally as a "pull tab," but this needs improvement as it can lead to damage of the tab that must also guide a strap and may also be inconvenient due to its location, as the tab could catch on objects, further causing damage and inconvenience and making long term use difficult.

Orthopedic devices often comprise a patella support for maintaining the patella in position to prevent dislocation. However, patella supports are frequently ineffective at holding the patella in position as the patella supports themselves, which often take the form of a pad attachable within a tubular body, are prone to migration or translation along a user's skin. Patella supports also can create pressure points or be inflexible, which further adds to user discomfort.

Flexible orthopedic devices often do not account for or properly address the compressive, supportive, restrictive, elastic, or breathability requirements of various distinct areas on a limb. As a result, they may provide too much compression and too little breathability in some areas while not providing enough compression in others. Such devices may fail to treat various pathologies or user-specific conditions properly.

There is seldom a solution that marries the benefits of a sleeve and a more rigid orthopedic device. Rather compromises are made with either a sleeve lacking sufficient properties to treat more severe injuries, rehabilitation and/or corrective action, and rigid orthopedic devices that may be uncomfortable, creating skin irritation and migrating over a user's leg.

From the preceding discussion, there is a need for a solution that offers improved migration control, comfort, and functionality, while being easier to don/doff and providing enhanced biomechanical support of a joint, such as by properly locating straps and providing effective patella support, and properly arranging areas of required elasticity and/or restriction.

SUMMARY

According to the disclosure, a sleeve is arranged for intimately fitting the limb and joint of the user and solves the problem of rigid braces and supports deterring a user from proper use and not facilitating joint motion activities. The sleeve is arranged to be worn with an orthopedic device, and lock therewith. The sleeve solves the problem of orthopedic devices, including flexible orthopedic devices and sleeves, having ineffective migration control and being difficult to don/doff, by serving as an interface between the user's leg and the orthopedic device.

The sleeve may have bands or regions integrated and/or attachable into the device's construction to restrict and guide the joint, and cooperate with the orthopedic device. These bands may be formed from metallic yarns, fusible, textiles, thermoplastic fibers, elastics, or other suitable materials and elements. The bands may be knit or inlayed during construction of the fabric brace, or mounted externally of the brace; alternatively, they may be modular and attachable to the device or components thereof for each adaptation in the initial installation use.

The sleeve's embodiments define a compliant, yet comfortable garment arranged to biomechanically provide motion restriction/facilitation of a joint or body segment. The embodiments are preferably adjustable in functional capacity to match a user's treatment plan's biomechanical requirements throughout rehabilitation. The sleeve may include various comfort factors to facilitate maximal compliance of the user throughout their treatment, such as profile, breathability, compression, flexibility, and rigidity.

The sleeve may be functionally knit. The sleeve may be provided with zones of different elasticity or devoid of elasticity, toughness, durability, and compressibility. The knitted structure of the sleeve has varying zones of compressibility serving as padding, which zones can be provided with other components, such as straps. For example, the sleeve may define at least two zones whereby the first zone has a more compressible knitted structure over which straps extend. In the second zone, the knitted structure may be thinner and more elastic than the first zone not to inhibit the movement of the orthopedic device about the user. Embodiments are provided with zones of differing elasticity to offer improved support and migration control over existing devices.

The sleeve is configured with a locking cuff, preferably located at a proximal end, adapted to fold over a proximal portion of the orthopedic device. The sleeve's exterior surface at the locking cuff may include a tacky material and/or band arranged to frictionally engage the exterior surface of the orthopedic device after the locking cuff is folded over the proximal portion of the orthopedic device. Therefore, unlike in prior art sleeves, the tacky band is disposed about an exterior circumference of the sleeve, and rather than the tacky band engaging with the skin of a user, it is used to engage the orthopedic device to inhibit migration over the user's leg during movement of the leg.

The sleeve may be advantageous for various orthopedic devices, as it may be arranged irrespective of the orthopedic device. The sleeve may be sized and dimensioned to extend proximally and distally of orthopedic devices. Alternatively, the sleeve may be sized and dimensioned to correspond to a particular type of orthopedic device. For example, it may have anatomical bands disposed of thereabout to accommodate both anatomical portions of a leg. Straps and frame members of an orthopedic device are provided to inhibit migration and augment the orthopedic device's efficacy, yet when combined with a sleeve, the sleeve can better distribute compressive and tensile forces on the user's leg exerted by the straps and frame members. For example, the anatomical bands may correspond to a user's knee and offer additional support to the knee in combination with the frame members and/or straps of the orthopedic device.

The sleeve may advantageously offer proprioceptive properties to the user, thereby compressing the leg about which the sleeve secures. The sleeve is breathable, as it is preferably a knitted textile structure, and securely fits the leg through the inherent elasticity of the sleeve and/or with bands displaced thereabout, such as at the proximal and distal ends, even with the locking band folding over to engage the frame of the orthopedic device. The proprioceptive properties may improve compliance in wearing the orthopedic device by offering improved comfort.

In an exemplary embodiment, the locking band's migration control comprises a frictional material placed about and/or on a knitted structure of the sleeve or in sections at a predetermined location or locations of the sleeve, such as a top or proximal end. The frictional material is preferably deposited and permanently secured along the exterior surface of the sleeve. The frictional material may be arranged in a pattern to provide breathability but balance tackiness and friction against a user's skin with comfort.

The sleeve is arranged with a cuff that bears the frictional material and can be folded over onto the orthopedic device to lock it therewith. The orthopedic device's surface texture or material is arranged to assure a secure fit with the sleeve's frictional material. The sleeve is donned before donning of the orthopedic device. Upon reaching the orthopedic device's desired location over the sleeve and concerning the user, the cuff can be folded to a position allowing for engagement of the frictional material against the orthopedic device. The sleeve may include appropriate markings or indicia to guide a user to the extent the sleeve is to be folded to facilitate donning and subsequent engagement of the frictional material against the orthopedic device frame.

In these and other possible embodiments, an orthopedic device's problems being ineffective at migration control with improved comfort are addressed and mitigated by the sleeve embodiments.

DESCRIPTION OF THE DRAWINGS

These and other features, aspects, and advantages of the present disclosure will better understand the following description, appended claims, and accompanying drawings.

FIG. 3A is a schematic view of a kit comprising an embodiment of the sleeve and an exemplary orthopedic device.

FIG. 3B is a schematic view of the sleeve of FIG. 3A being donned on a user's leg.

FIG. 3C is a schematic view of the sleeve of FIG. 3A donned on a user's leg.

In the figures, similar elements are provided with similar reference numbers. The drawing figures are not drawn to scale or proportion but instead are drawn to understand the components better and are not intended to be limiting in scope but provide exemplary illustrations.

DETAILED DESCRIPTION OF VARIOUS EMBODIMENTS

A. Fabrication of Various Embodiments

Figure 1:
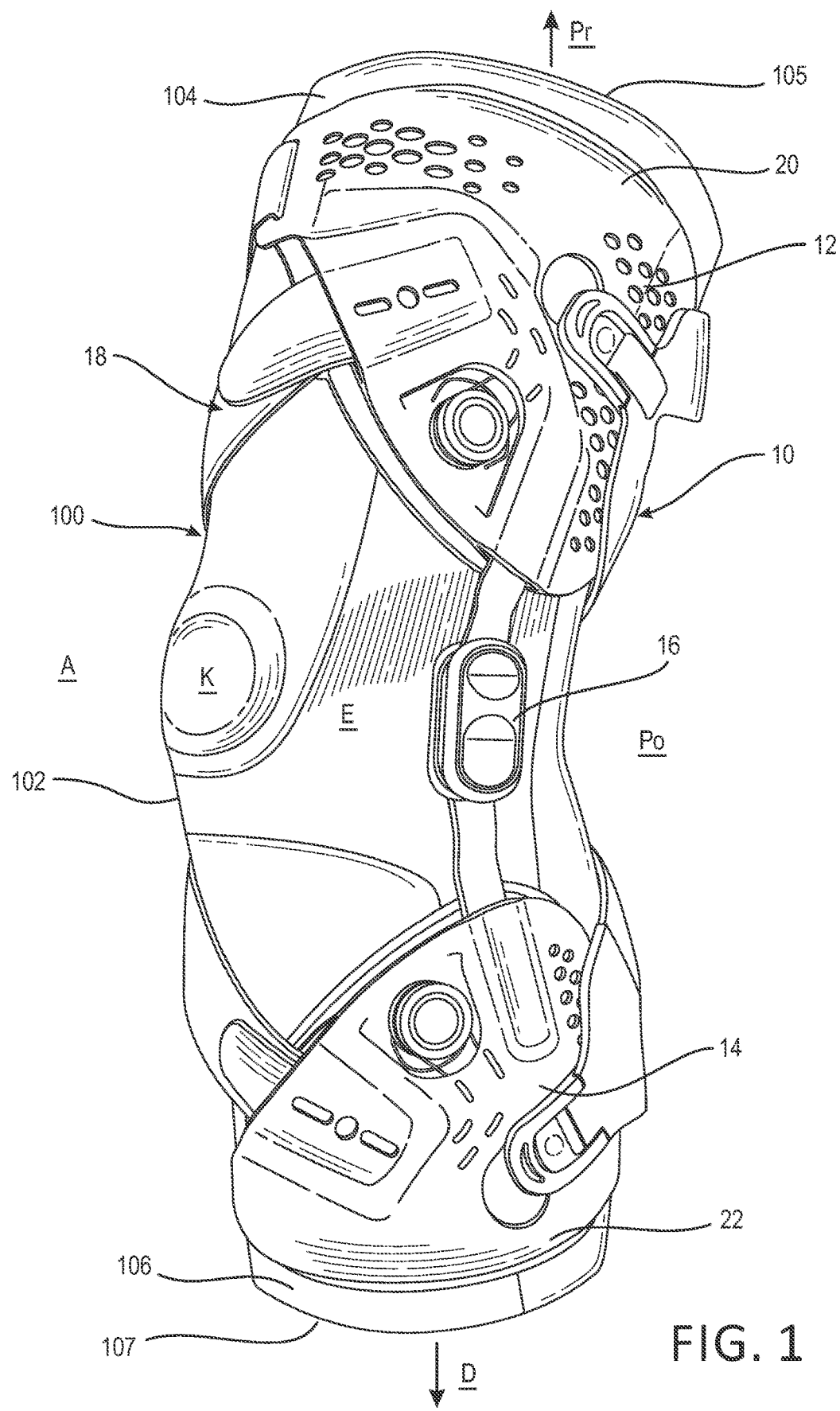
FIG. 1 is a perspective view of an embodiment of the sleeve in combination with an exemplary orthopedic device.

The sleeve is preferably functionally knit, with different properties extending along its length, and the sleeve may likewise be knitted with different yarns to obtain such functional features. The sleeve may be formed as explained in U.S. Pat. No. 10,758,393, issued on Sep. 1, 2020, U.S. Pat. App. Publ. 2019/0142620, published on May 16, 2019, and U.S. Pat. App. Publ. 2019/0105188, published on Apr. 11, 2019, each incorporated herein by reference.

Various embodiments of the sleeve may utilize flat knitting, which allows the production of textile structures into a final desired shape, so there is no cutting and very minimal waste. Flat knitted elements are formed directly in the desired three-dimensional shapes or modular panels, which can help avoid the need to use additional support structures. The sleeve embodiments may be constructed as taught in U.S. Pat. App. Publ. 2019/0142620, including the different bands or regions having different elasticities and the coating of the knitted sleeve with a frictional material.

Several desired performance characteristics can be localized into performance zones in engineering the stitches to stretch, restrict, pad, or contour to body shapes, using multiple types of yarns and/or combined stitch patterns at strategic placements within a single, unitary construction. The knitting can form various pockets, channels, and tunnels to introduce restrictive stays, pads, hot/cold packs, hyperelastic materials, inflatable pouches (liquid or air), webbing, hardware, and/or other customizable elements of bracing and support. Inflatable areas in the knit pouches can exert pressure and force on the desired areas and are customized to a patient's condition.

Embodiments of the sleeve preferably may be formed from a knitted textile support having a shape created on a knitting loom including, but not limited to, various warp knitting, circular knitting, or weft (flat) knitting processes. Embodiments of the sleeve may take the form of a garment. Support areas may include several textile elements combined into one textile support panel with unitary construction or a group of modular panels for treating a medical indication. The textile panel or panels' body provides a biomechanical range of motion, compression, and therapeutic elements integrated into a single panel or panels that may form a garment. Three-dimensional flat knitting allows the production of these textile structures into a final desired shape to avoid cutting and waste.

Each panel or series of panels may have areas of gradient levels of stretch, flexure, rigidity, and restrictive elements integrated into the fabric by mapping the levels of motion or restriction required for a medical indication. These possible configurations may be achieved through a corresponding knit stitching technique system that starts with yarns.

Knit stitching techniques create varying degrees of elasticity, rigidity, open channels, tunnels, and intarsia zones of specialized yarns integrated into the base fabric. The first area of knitting may be formed of a first stitch configuration, and the second area may be formed of a second stitch configuration different from the first stitch configuration to impart varying textures or properties to a surface of the textile element. These properties may include anti-bacterial, cooling, warming, elasticity, rigidity, compression, wicking, and/or color.

The knitted base of the sleeve can comprise natural and/or synthetic yarns: silk, wool, polyester, nylon, olefin, and interlaced with specialty yarns: moisture management, elasticized, fusible, metallic, Kevlar, silicone, and other types of performance yarns knit into fully fashioned, textured, intarsia, or three-dimensional regions and appendages such as connected tubes, circles, open cuboids, straps, spheres, and other integrated knit shapes.

Flat knitted elements may be formed directly in the desired three-dimensional shapes or modular panels, which can help avoid the need to use additional support structures and emerge from the machine ready to be sewn together, saving on manufacturing costs. This fully fashioned knitting technique adds or drops stitches to create custom two- and three-dimensional shapes appropriate to the desired finished garment structure.

The intarsia areas may comprise threads or yarns isolated into specialized zones, using silicon, Kevlar, fusible, nylon monofilament, Dynema, spandex, and/or other specialty performance yarns knit into the fabric to enable that region to perform a function. These areas can be arranged into any flat, textured, or three-dimensional shape required for load mapping the garment for the medical indication.

The load mapped zones may be further achieved by combining knit structures (knit, tuck, miss), transferring loops, dropping or adding needles, segmenting takedown in varying rates across the width of the garment fabric, varying structural elements, inlaying yarns, weft insertion, direct feed, warp insertion, and the varying speed of yarns fed into the system. Besides standard knitting feeders, several types of specialized knitting feeders may isolate, apply, and integrate these yarns into the base fabric of this garment: intarsia feeders, in-lay, direct feeders, and plaiting feeders. With the plaiting, the yarn may lie in the isolated area but only on the face or the back of the fabric.

B. Biomechanics of Various Embodiments

Control of joint range of motion includes motion inhibition, restriction, or prevention. The control may be obtained through altering the tension in a garment on a tangent to the skin controlling motion through shear loads (at a tangent to the skin). Control of joint range of motion and soft tissue may be assisted through compression or loading, at or near a normal direction to the skin and/or garment's surface.

In embodiments of the sleeve, the normal motion may be disrupted by an intimately fitting garment with restrictive bands integrated therein for constructing the sleeve. The restriction may be created by altering both the yarn and the weave of the fabric. The interface between fabric and skin can vary. Some areas can be low stretch and have high friction or tackiness bonding the fabric to the skin. These regions form an anchor for the stabilization of the garment to the core and the extremity.

Other textile areas can have high stretch and offer low friction, allowing the body segment to move freely. By carefully selecting the anchor zones and orienting restrictive bands within the textile, embodiments can restrict or guide the joint in question, preventing injurious movement and even encouraging safe motion strategies about the joint.

Some zones may provide greater compressibility or padding than others and may be arranged with the sleeve components. For example, certain zones may have greater compressibility brought by the knitted structure or simply the physical structure, as in a greater thickness. In addition, these zones may have overlapping or integrated elements, such as straps, hinges, stays, and other common brace components. The zones of greater compressibility provide protection and comfort to the user by mitigating the user's exposure of the components and their interaction with the movement of the sleeve.

C. Definitions

An exemplary orthopedic device may be found in U.S. Pat. App. Publ. 2019/0105188. The orthopedic device embodiments may serve in protective, preventative, or remedial capacities. While the orthopedic device is described within a preferred embodiment directed to the knee, many of the features described herein may be extended to various orthopedic devices and components that secure other joints and body parts.

The orthopedic device embodiments and components for use with the sleeve may be dimensioned to accommodate different types, shapes, and sizes of human joints and appendages. Embodiments of the sleeve may be modified to orient principal forces exerted by strap systems of the embodiments at any desirable location to secure the device onto a leg to stabilize the joint.

The knee joint comprises lateral and medial joints between the femur and tibia and one arthrodial joint between the patella and femur. The primary movements of the knee comprise flexion, i.e., rearward rotational movement of the tibia relative to the femur (the completion of flexion ideally resulting in a fully bent leg), and extension, i.e., forward rotational movement of the tibia relative to the femur (the completion of extension ideally resulting in a fully straightened leg).

For explanatory purposes, each orthopedic device and sleeve embodiment or component thereof described herein may be divided into sections denoted by general anatomical terms for the human body. Such anatomical terms are provided to distinguish various elements of the device embodiments from one another but are not to be considered to limit the scope of the disclosure.

For example, these terms may be used about a human leg, which is divided into similar sections with a proximal-distal plane generally extending along with the knee's meniscus between the femur tibia. The terms "proximal" and "distal" generally refer to locations of the device that correspond to the location of the leg relative to the point of attachment of the leg to the body. The terms "upper" and "lower" may be used in combination with "proximal" and "distal" to connote gradations in the location of "proximal" and "distal." The location where the device corresponds to the knee joint is used herein to delimit the proximal and distal sections of the device generally.

The embodiments of the orthopedic device and sleeve can also be considered to fall within "anterior" and "posterior" sections of an anterior-posterior plane. The anterior-posterior plane generally corresponds to the coronal or frontal plane of a human leg, which lies along the central longitudinal axis of a body (for exemplary purposes, the longitudinal axis X-X in FIG. 2). Therefore, a posterior side or element is located behind this anterior-posterior plane, whereas an anterior side or element is located in front of the anterior-posterior plane.

The terms "inwardly" or "inner" are commonly used herein to distinguish the side of the device that may be directed to the posterior side of the device and specifically adjacent to the leg of the device's wearer. Contrariwise, the term "outwardly" or "outer" denotes the side of the device that is opposite to the inward side.

The terms "medial" and "lateral" are relative terms that are generally understood as indicating location concerning the midsaggital plane or midline. Therefore, elements near the midline are referred to as "medial" and those elements that are further from the midline are considered to be "lateral." The term "central" denotes the area along the midline of a joint, thereby dividing and sharing regions of the medial and lateral regions.

The terms "rigid" and "flexible" may distinguish characteristics of portions of certain features of the orthopedic device and the sleeve. The term "rigid" should denote an element of the device is devoid of flexibility. Within the context of the frame or support members or shells that are "rigid," it should indicate that they do not lose their overall shape when force is applied, and they may break if bent with sufficient force. The term "flexible" should denote that features are capable of repeated bending such that the features may be bent into retained shapes or the features retain no general shape but continuously deform when force is applied.

The term "adjacent" means one element is continuous or directly connected to another element, thereby sharing a border.

The term "continuous knit" and its immediate variants such as "continuously knitted" means a textile having a continuous knit face without integrally formed or engineered openings (e.g., without intentionally dropped or transferred stitches) or seams. Examples would include a single jersey knit construction, a half tricot knit construction, a double jersey knit construction, and the like.

The term "cuff" is considered an end part of the sleeve at at least one of the open ends, whereby the material of the sleeve at the cuff is capable of being turned back.

The term "discrete" means a finite area that does not overlap another site or portion or region.

The term "elastic" means being capable of recovering in size and shape after deformation. In the instance of a cuff of a sleeve, the cuff may be deformed by enlarging its circumference by exerting force or resisting as it is enlarged to fit over a limb and returning to its initial state without the exertion of force or resistance to a larger shape.

The terms "integral" or "integrally knit" or "integral construction" mean that components are secured to, formed with or joint to, and function as a single article in one piece. "Integral" by itself means being manufactured together simultaneously; that is, being made together as one part and not two separately manufactured parts. "Integral" also means at least one textile element that extends between different textile and/or sleeve areas.

The term "knit" means having been formed by interlacing yarn or thread in a series of connected loops.

The term "mesh" means a textile having a knit construction where openings are created by modifying the knitting process used to form the textile (e.g., by dropping or transferring stitches).

The term "pressure-sensitive adhesive" means a nonreactive adhesive that forms a bond when pressure is applied to bond the adhesive with a surface. No solvent, heat or water is needed to activate the adhesive. The pressure-sensitive adhesive forms a bond and holds properly at room temperature, and the degree influenced by the amount of pressure.

The term "sleeve" is accorded its ordinary meaning as a tubular part arranged to fit over a limb, whether an arm or leg, and at any portion of such arm or leg. The sleeve is defined as having first and second opposed open ends, in which either end can accommodate a portion of an arm or leg.

The term "textile" means a woven or knit fabric formed from interlocking fibers, filaments or yarns. The term "fabric" may be made through weaving, knitting, spreading, felting, stitching, crocheting or bonding that may be used in the production of further products.

The term "tacky" means sticky to the touch and is provided by material properties of a material. 'Tack' is the measure of initial grab or stickiness of an adhesive tape or substrate without or light the application of pressure.

D. Detailed Description of Various Embodiments

Referring to FIG. 1, an orthopedic device 10 is arranged as a knee brace, with the depicted exemplary embodiment being an osteoarthritis brace according to U.S. Pat. App. Publ. 2019/0105188, and provided in combination with a sleeve 100 according to the invention. While the embodiment of the orthopedic device in FIG. 1 depicts an osteoarthritis brace, the sleeve 100 may be used with other types of knee braces.

The sleeve 100 includes a main body panel or main panel or main body 102 arranged in this embodiment as a knit tubular sleeve having first or proximal and second or distal regions 104, 106. The first and second regions 104, 106 are continuously knit to one another to maintain a structure without interruptions.

The first and second regions 104, 106 are integral and continuously knitted with the threads or yarns interwoven to one another rather than forming sections stitched to one another by additional threads or yarns and/or seams. While integrally knit to one another, the first and second regions 104, 106, and the main body 102 may be considered discrete relative to one another because they are demarcated relative to one another by their properties elasticity and/or color. Alternatively, the main body 102, and the first and second regions 104, 106 may gradually transition into one another due to sharing certain properties of their knit, including shared elastic yarns. While in this embodiment the main body 102 is arranged as a tubular sleeve, other configurations and shapes may be suitable, with the tubular sleeve being dimensioned and configured according to the intended anatomy upon which the sleeve is donned.

The sleeve 100 defines a locking cuff 108 arranged to fold over and engage a first or proximal frame portion 12 of the orthopedic device 10. By engagement, it is intended that the locking cuff 108 frictionally secures against the first frame portion 12 to prevent movement between the first frame portion 12 and the locking cuff 108. This arrangement inhibits migration or movement of the orthopedic device 12 on the user's leg as the sleeve elastically engages the user's leg and engages with the orthopedic device 12 to keep the leg, sleeve and orthopedic device in a locked configuration with one another.

Figures 2A, 2B:
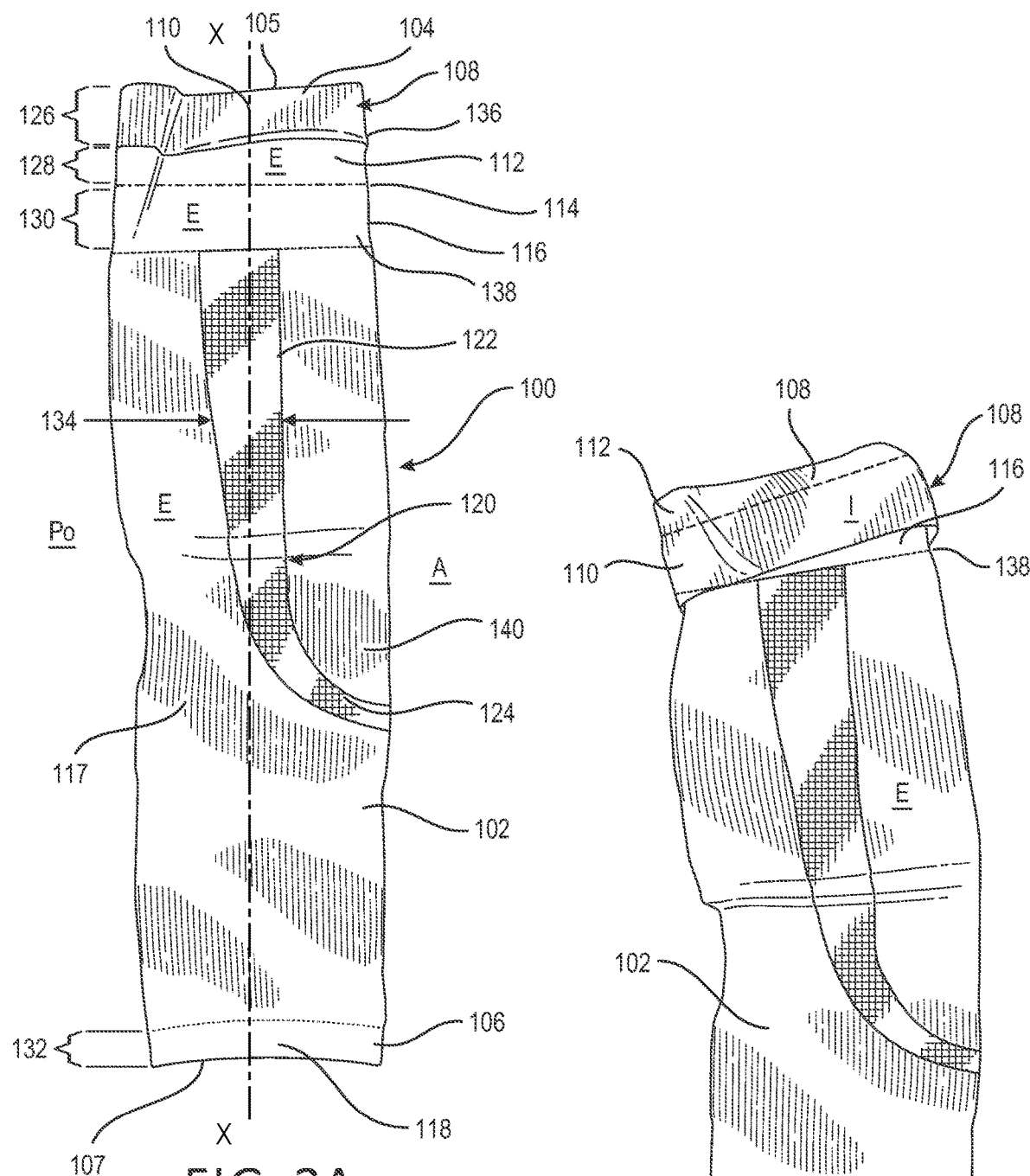
FIG. 2A is a schematic elevational view of an embodiment of the sleeve in an unfolded configuration.
FIG. 2B is a schematic elevational view of the sleeve in FIG. 2A in a folded configuration.

The locking cuff 108 extends over at least a first edge 20 of the first frame portion 12, and elastically secures over the frame portion 12 by enlarging in circumference to a fitted circumference and returning to an initial circumference without enlarging, as would be the case in the embodiment and state of FIG. 2A.

The selection of a material disposed about the locking cuff 108 is selected to enhance the resistance of movement of the locking cuff 108 to the exterior surface of the first frame portion 12. The material on the locking cuff is arranged to rub against the exterior surface and form a frictional connection. The locking cuff is held in place due to frictional forces that resist relative movement between the frame locking cuff. Such frictional forces are in contrast when compared to simply rubbing the textile, without the frictional material, of the sleeve against the first frame portion, which likely provides minimal frictional resistance to movement relative to one another.

FIG. 1 depicts the sleeve 100 being longer than the orthopedic device 10. The orthopedic device has the first frame portion 12 and the second frame portion 14 connected by a hinge 16, including a strap assembly 18. An entirety of the orthopedic device 10 extending over the sleeve 100, with the first and second regions 104, 106, particularly the proximal edge 105 and the distal edge 107 extending in the proximal and distal directions Pr, D beyond a first or proximal edge 20 and a second or distal edge 22 of the orthopedic device 10. The sleeve length 100 minimizes possibly chaffing as the interface underneath the orthopedic device is taken up by the entirety of the sleeve, even if the orthopedic device includes conventional padding (not shown).

FIG. 2 illustrates the sleeve 100 having the locking cuff 108, which includes a tacky band 110 extending along with the exterior surface E of the sleeve 100. Particularly, the tacky feature or material of the tacky band 110 only extends about the exterior surface E of the sleeve 100 in that the tacky feature or material of the tacky band 110 is not present on an interior surface I of the sleeve 100. According to the depicted embodiment, the tacky band 110 extends completely about the circumference of the sleeve 100. Alternatively, the tacky band 110 may be defined by circumferential segments, each spaced apart by one another, or the tacky band 110 is defined by a collection or pattern of tacky elements. In another variation, the tacky band 110 may be arranged in locations corresponding to the shape of the first frame portion 12 of the orthopedic device.

The tacky band 110 may be formed from silicone or other suitable tacky and frictional material deposited and permanently secured to the elasticized textile material of the sleeve, forming a first textile band having the height 126. The first textile band underlying the frictional material may have localized elastic properties contrasting to other elastic properties of the sleeve 100 in that the first textile band may have greater elasticity to securely position the tacky band about the orthopedic device, such that the increased elasticity improves the frictional properties. The receiving band and the distal band may be knitted with any of the aforementioned yarns and knitted structures to adapt the sleeve to desired elasticity at such portions of the sleeve.

The level of tackiness it not intended to damage the substrate or surface upon which the tacky band contacts. It is intended that the level of tackiness is selected to permit repeated holding of the tacky band to a surface and removal therefrom without damage to the tacky band and the surface. The silicone may serve as a pressure-sensitive adhesive, and the adhesion and tack may be dependent on the thickness and formulation of the silicone on the first textile band. The silicone pressure-sensitive adhesive may be selected upon a variety of criteria, as shown, by example and in a non-limitative manner, in "Choose Dow silicone PSA for high performance," published in 2019 by the Dow Chemical Company, and incorporated herein by reference.

The tacky band 110 defines a distal edge 136 at which it interfaces with a non-tacky band 112 of the locking cuff 108, located distally from the tack band 110. A thickness of the sleeve 100 may be greater at the tacky band 110 than the non-tacky band 112, inclusive of a tacky or frictional material disposed on the textile material, with the tacky material and the textile material combining to form the tacky band 110. The frictional material may inhibit the elasticity of the underlying textile material of the tacky band 110, thereby providing a securer compressive portion of the sleeve when folded over the orthopedic device.

The tacky band 110 may define the proximal edge 105 of the first end 104 and has a height 126. While there is no preferred height 126, it may be modified according to the degree it is desired to include frictional material about the tacky band 110. The non-tacky band 112 has a height 128 combining with the tacky band 110 generally a same height as a height 130 as the receiving band 116, or the height 128 of the non-tacky band 112 and/or or a height 130 of the receiving portion, each being greater than the height 126 of the tacky band 110.

The locking cuff 108 includes the tacky band 110 and a non-tacky band 112 located adjacent to and distal from the tacky band 110. According to a variation, the non-tacky band 112 is formed from a second textile band having the height 128. The first and second textile bands 110, 112 may have different elastic properties or possess the same elastic properties.

The locking cuff 108 terminates distally at a fold-line 114. The fold-line 114 may comprise a stitching or coloring distinguishing the locking cuff 108 from a receiving band 116 along the sleeve length relative to a central longitudinal axis X-X of the sleeve 110, as depicted in FIG. 2A. The receiving band 116 preferably extends adjacently and distal from the non-tacky band 112. The receiving band 116 and the non-tacky band 112 may have the same or different elastic properties. The receiving band 116 is demarcated along its distal edge 138 from a central tubular portion 117 of the sleeve body 102.

The sleeve body 102 defines a distal band 118 having different elastic properties than the central portion of the sleeve 117. The distal band 118 preferably has a height 132 less than the height of the tacky band 110.

A central portion 117 of the sleeve body 102 is preferably defined between the receiving band peripheral edge 138 and the distal band 118 includes an anatomical band 120 arranged to contour a user's anatomy. The anatomical band 120 has different elastic properties than portions of the central portion 117 outside of the anatomical band 120.

The anatomical band 120 defines a lateral/medial band 122 arranged to extend generally between and directed along with at least one lateral or medial side of a user's leg. The lateral/medial band 122 is arranged to extend proximal of the knee. The lateral/medial band 122 may taper in width 134 as it approaches a knee portion 140 of the sleeve. The lateral/medial band 122 extends to the distal edge of the receiving band 138 and has the greatest width thereat.

The anatomical band 120 defines a knee band 124 continuously extending from the lateral/medial band 122 along a first medial or lateral side of a user's leg and is adapted to generally extend transversely from the lateral/medial band 122 and arranged to correspond to a knee. The knee band 124 preferably extends distal of the knee. The knee band 124 may symmetrically extend distally of the knee and/or may be asymmetrical extending continuously to a second lateral/medial band 142 extending along an opposite lateral or medial side of a user's leg.

As shown in FIGS. 3B and 3C, the knee band 124 extends or dips below a centerline 146 of the sleeve 100 generally corresponding to a user's knee's centerline. The lateral/medial band 122 has a proximal portion 143 and a distal portion 144 alongside the same lateral or medial side of the user's leg. The knee portion extends arcuately from the proximal and distal portions 143, 144 of the lateral/medial band 122. A first side of the anatomical band 120 defines proximal and distal portions 143, 144 and a second side of the anatomical band 120 defines only a proximal portion 142.

The proximal and distal portions 143, 144 correspond to first and second frame portions 12, 14, respectively, and the hinge assembly 16 of the orthopedic device 10. In a variation, the anatomical band 120 may define portions corresponding to the strap assembly 18. The opposite medial/lateral band 142 may be arranged to counteract or facilitate the donning of the sleeve according to its elastic properties. In another variation, the sleeve body 102 has at least one knitted structure adapted to resist sliding of the orthopedic device 12 thereon.

The locking cuff may include fiber or fiber combination or yarns comprising Tencel, polyimide and Lycra, and may be rib knitted. The locking cuff may have a knitted structure that imparts greater elasticity and yarns that offer greater elasticity, as specified. The tacky or frictional material may be silicone which is inherently tacky and offers improved frictional properties over the knitted structure underlying the tacky or frictional material. The tacky or frictional material may impregnate the knitted structure to securely integrate with the knitted structure. Due to tacky or frictional material having greater resistance to elasticity than the underlying knitted structure, the tacky band can pressure the orthopedic device when in a folded configuration.

The non-tacky band may be similarly knitted as the underlying material in the tacky band, yet because it is not coated on the exterior surface, it has greater elasticity, which may be advantageous as it may extend over and be more compliant to the proximal edge of the orthopedic device. By extending the non-tacky band at the foldline over the proximal edge, thereby clearing the tacky band over the proximal edge, the tacky band can be focused on provide radial tensile forces about the orthopedic device. The The sleeve body may be constructed with a knitted structure including Tencel, polyimide and Lycra with some polyester. The sleeve body's knitted structure may include the anatomical band, which may have added yarns of different types or be stitched differently than areas of the sleeve body outside the anatomical band. The anatomical band is preferably knitted with yarns of a different color than the sleeve body to offer guidance on the sleeve placement. The sleeve body may have a patella region, i.e., the demarcated zone with the knee indicia 148 in FIGS. 3B and 3C, knitted with differently colored yarns and with a structure to improve elasticity at the knee. Likewise, although not shown, the popliteal region behind the knee may include a mesh to improve breathability.

Figure 3D:
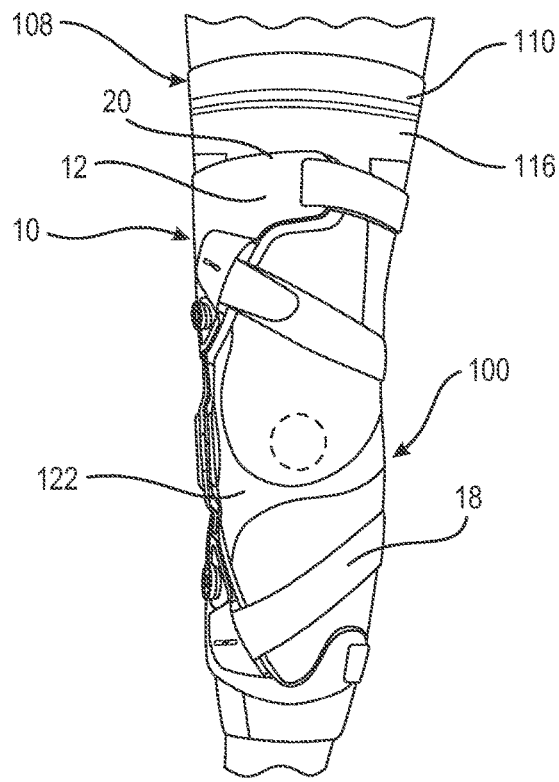
FIG. 3D is a schematic view of the donned sleeve of FIG. 3C in an unfolded configuration with the exemplary orthopedic device.

FIGS. 3A-3F generally show the method for donning the sleeve over the leg of the user in combination with the orthopedic device. FIG. 3A shows a kit comprising the orthopedic device 10 and the sleeve 100 for placement over a user's leg L and knee K.

FIG. 3B illustrates the user pulling the first end portion 104 of the sleeve 100 in a proximal direction Pr over the user's leg to proximate the sleeve 100 over the knee K about the center line 146. The center line 146 is illustrated for exemplary purposes to show the proper positioning of the sleeve. The anatomical band 120 is lined up according to the knee K and possesses the aforementioned portions corresponding to the user's leg L and knee K. Of note, the sleeve 100 pulled onto the leg L in an unfolded configuration with the locking cuff 108 unfolded. The user may use the grip provided by the frictional material to hold the sleeve 100 as it is donned on the leg. The sleeve 100 may define indicia 148 that corresponds the patella or knee K of the user to assure proper placement of the sleeve over the leg L.

FIG. 3C illustrates the sleeve 100 donned on the leg and lined up according to the knee K, with the anatomical band 120 lined according to the user's leg. The locking cuff 108 is unfolded.

FIG. 3D illustrates the orthopedic device 10 lined up relative to the locking cuff 108 and the anatomical band 120. The locking cuff 108 is still in the unfolded configuration until the orthopedic device 10 is properly donned and lined up with the sleeve 100.

Figure 3E:
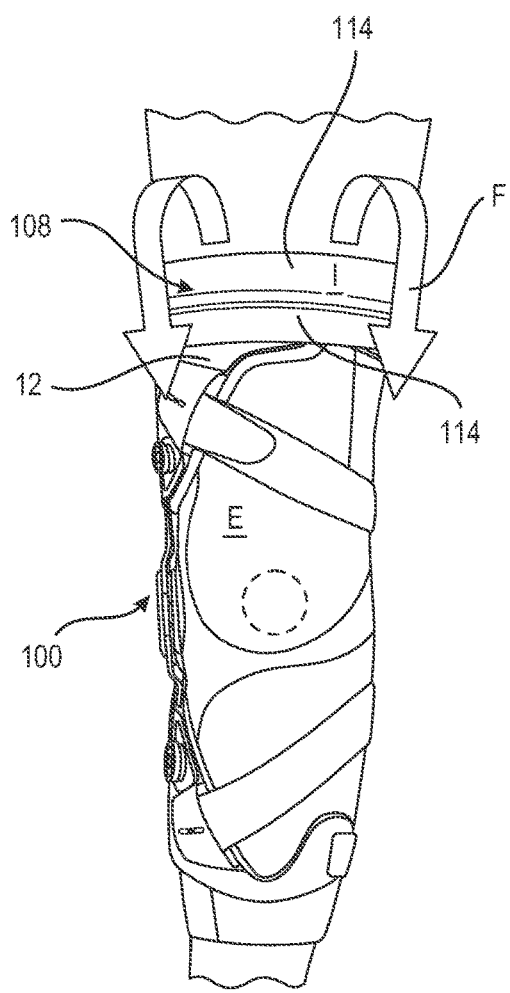
FIG. 3E is a schematic view of the sleeve of FIG. 3A being folded into the folded configuration over the exemplary orthopedic device.

FIG. 3E illustrates the folding of the locking cuff 108 at the foldline 114 over the exterior surface E of the orthopedic device 10. The interior surface I of the locking cuff 108 is exposed and the exterior surface E of the locking cuff 108 frictionally engages the first frame portion 12 of the orthopedic device 10.

Figure 3F:
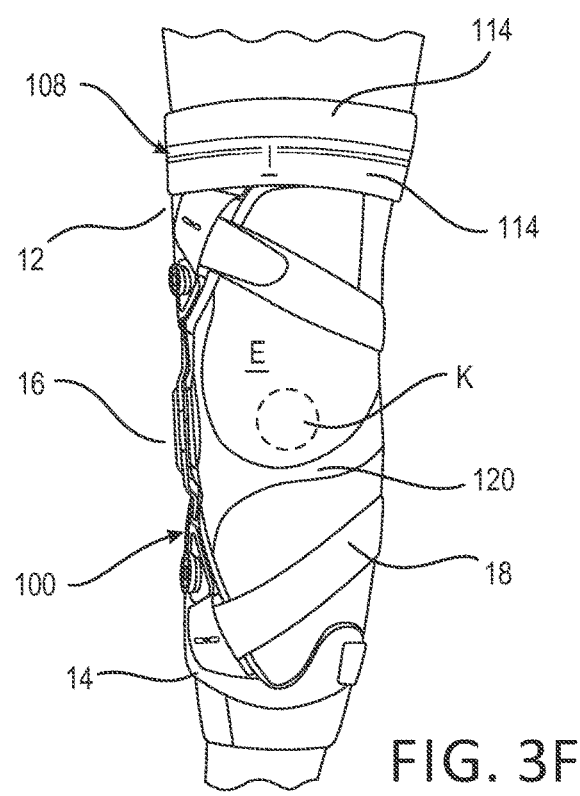
FIG. 3F is a schematic view of the sleeve of FIG. 3A in the folded configuration and locked with the exemplary orthopedic device.

FIG. 3F illustrates the sleeve 100 with the locking cuff 108 in the folded configuration. The first and second frame portions 12, 14, the strap assembly 18, and the hinge assembly 16 extend over the exterior surface E of the sleeve 100.

In any of the aforementioned embodiments and variations thereof, a sleeve may include straps or locking tabs for added function to the sleeve and connection to the orthopedic device. The straps can be external, or they may be knitted into the brace, or they can be knitted as zones of low elasticity into the brace.

For external straps, markers may be provided on the strap to guide the user on applying the strap or adjusting the cables for tensioning or reducing tension in the strap. The markers can be knitted into the knitting of the sleeve or otherwise applied, such as by heat transfer.

In another embodiment, straps or bands can be laminated into or over the sleeve. The sleeve may be knitted in a manner including zones of hook receivable material or structure, and the corresponding strap may include hook material for engaging the hook receivable zone. Loops may be formed directly by the orthopedic device for guiding the strap or cables.

It is possible to knit the sleeve so that the active components are visible on the inside, while the outside of the brace is more uniform in appearance. This ability enables the user to see how the sleeve functions before donning while not being "too flashy" when worn.

Not necessarily all such objects or advantages may be achieved under any embodiment of the invention. Those skilled in the art will recognize that the invention may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct a sleeve under principles of the present disclosure. Therefore, the embodiments described may be adapted to orthopedic systems to secure, support, or comfort limbs or other anatomy.

Although this disclosure relates to preferred embodiments and examples, it therefore will be understood by those skilled in the art that the present invention extends beyond the disclosed embodiments to other alternative embodiments and/or uses and obvious modifications and equivalents. It is intended that the scope of the present invention disclosed should not be limited by the disclosed embodiments described above, but should be determined only by a fair reading of the claims that follow.

The invention claimed is:

1. A sleeve, comprising:
a tubular body having first and second ends;
wherein the first end defines a locking cuff having a tacky band extending about an exterior surface of the sleeve of the first end of the tubular body; a non-tacky band located extending distally from the tacky band relative to a longitudinal axis of the sleeve; and a receiving band located extending distally from the non-tacky band relative to the longitudinal axis;
wherein the tacky band has a first height relative to the longitudinal axis and the non-tacky band has a second height relative to the longitudinal axis combining to a height that is the same as a third height of the receiving band relative to the longitudinal axis;
wherein the tacky band only extends about the exterior surface of the sleeve in that the tacky band is not present on an interior surface of the sleeve;
wherein the tubular body further defines a central portion adjacent to and extending distally from the receiving band relative to the longitudinal axis to the second end.

2. The sleeve of claim 1, wherein the tubular body is formed from an elasticized textile.

3. The sleeve of claim 1, wherein the central portion includes an anatomical band adapted to a contour of an anatomy of a user, the anatomical band has at least one different elastic property different from an elastic property of the central portion.

4. The sleeve of claim 1, wherein the central portion includes indicia configured to correspond to a knee of a user.

5. The sleeve of claim 1, wherein at least one of the tacky band, non-tacky band and the receiving band has a different elasticity from one another.

6. The sleeve of claim 1, wherein the tacky band extends completely about a circumference of the sleeve.

7. The sleeve of claim 1, wherein the tacky band is defined by a pattern of tacky elements arranged about an underlying material segment of the tacky band.

8. The sleeve of claim 1, wherein the tubular body defines a distal band adjacent to a distal end of the central portion, the distal band has elastic properties different from that of the central portion.

* * * * *